United States Patent
Kornefeld

Patent Number: 5,423,841
Date of Patent: Jun. 13, 1995

[54] INTRAOCULAR KNIFE

[76] Inventor: Michael S. Kornefeld, 10332 Sannios, Apt. 5, St. Louis, Mo. 63146

[21] Appl. No.: 212,932

[22] Filed: Mar. 15, 1994

[51] Int. Cl.⁶ .............................................. A61B 17/32
[52] U.S. Cl. ..................................... 606/166; 606/167
[58] Field of Search ............. 606/166, 167, 170, 180, 606/205–211; 30/388, 389, 505, 321

[56] References Cited

U.S. PATENT DOCUMENTS

| | | | |
|---|---|---|---|
| 1,492,553 | 5/1924 | Behrman | 30/321 |
| 4,180,075 | 12/1979 | Marinoff . | |
| 4,570,632 | 2/1986 | Woods . | |
| 4,706,669 | 11/1987 | Schlegel . | |
| 4,708,138 | 11/1987 | Pazandak . | |
| 4,766,896 | 8/1988 | Pao . | |
| 4,766,897 | 8/1988 | Smirmaul . | |
| 4,885,004 | 12/1989 | Pao . | |
| 4,911,161 | 3/1990 | Schechter . | |
| 4,955,894 | 9/1990 | Herman . | |
| 5,203,865 | 4/1993 | Siepser . | |
| 5,261,923 | 11/1993 | Soares | 606/166 |

Primary Examiner—Stephen C. Pellegrino
Assistant Examiner—William Lewis
Attorney, Agent, or Firm—Barnes & Thornburg

[57] ABSTRACT

An ophthalmic surgical device is provided for facilitating a continuous, smooth, curve linear, stress-free, tag-free cut of the anterior capsule which comprises a handle, a blade rotatably mounted to the handle's distal end and a controller on the handle for manually and positively positioning the blade at a desired angular position during movement of the handle.

10 Claims, 2 Drawing Sheets

U.S. Patent  June 13, 1995  Sheet 1 of 2  5,423,841
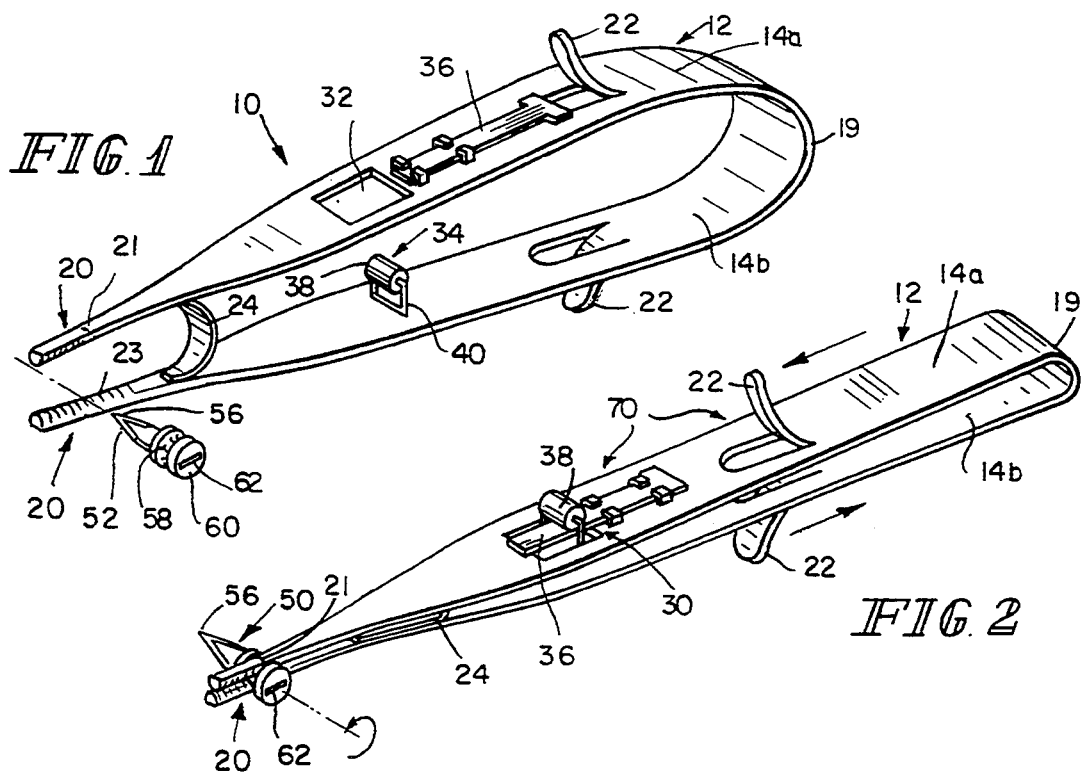
FIG. 1
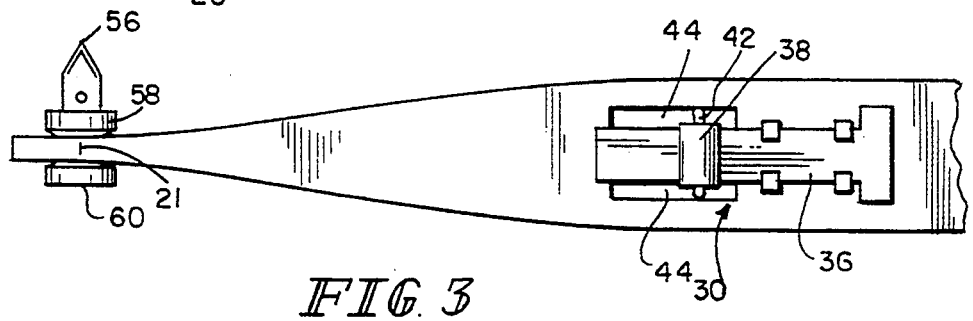
FIG. 2
FIG. 3
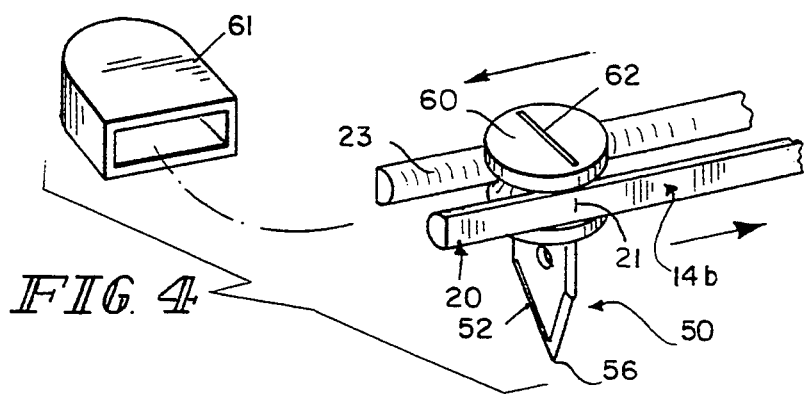
FIG. 4

INTRAOCULAR KNIFE

BACKGROUND AND SUMMARY OF THE INVENTION

This invention relates generally to a device for use in ophthalmic surgery with a specific application to intraocular surgery. This invention consists of novel features which will help a surgeon in performing surgeries on lens disorders such as cataracts. Specifically, the present invention relates to a surgical knife for making a continuous, smooth, curvilinear, stress-free, tag-free cut of the anterior lens capsule required in extracapsular cataract surgery. This invention is unique and novel in that it permits the surgeon to manually and positively position the blade at a desired angular position during movement of the surgical instrument's handle.

An individual's vision depends upon the eye forming an image of an object and sending that image to the sensory centers of the brain. Image formation involves the following process: an object will reflect light through the cornea, the aqueous humor, the pupil, the lens, and the vitreous humor of the eye; the reflective light is then focused by the lens onto the retina. The nerve fibers within the retina collectively leave the eye in the optic nerve and enter the brain where the visual signals are processed.

However, the lens and its ability to form an image is subject to physical damage due to lens disorders such as the formation of cataracts. Lens deficiencies, such as cataracts, are generally treated by performing cataract extraction wherein an opening is provided in the anterior lens capsule through which the lens opacity is removed. This procedure involves removal of the opaque crystalline lens substance after opening the anterior lens capsule by an anterior capsulectomy. The anterior capsule is a cellophane-like membrane covering the anterior surface of the lens.

A variety of devices have been created to cut or tear the anterior capsule. The most common device used today for an anterior capsulotomy is a cystotome. When cataracts are removed by an extracapsular extraction method, a cystotome is inserted through a small incision in the sclera or peripheral cornea and small connecting tears are made in the anterior lens capsule in a circular pattern around the periphery of the lens capsule. When a complete circle has been made by connecting the tears, a circular piece of the anterior capsule is free to be removed. For extracapsular cataract extractions, this method is sufficient and desirable.

The phacoemulsification method of cataract removal requires a different type of anterior capsular opening. During phacoemulsification, there is a great deal of tension on the cut edges of the anterior capsule while the lens nucleus is emulsified with ultrasound energy. For this method, a tagless, continuous cut or tear is a critical step for safe and effective phacoemulsification. If the capsule is opened with numerous small capsular tears, as in the extracapsular technique, the small tags which remain can lead to capsular tears which can extend posteriorly to the posterior capsule. Such a radial tear is a complication because it destabilizes the lens for further cataract removal and safe intraocular lens placement within the lens capsule later in the operation. More importantly, once the posterior capsule is punctured, the vitreous humor behind it gains access to the front of the eye. If the vitreous enters the front of the eye through a hole in the posterior capsule, the vitreous must be removed by an additional procedure with special instruments. This vitreous loss is associated with an approximate increase two times in the rate of subsequent retinal detachment and in increased risk of endophthalmitis or infection within the eyeball; both complications are potentially blinding.

The methods which are currently employed for producing a continuous curvilinear capsular opening are quite difficult to control by the surgeon. The standard method begins with a capsular incision which is made with a cystotome. This incision is then coaxed to form a circular or oval shape by pushing the leading edge of the freshly tearing capsule with the cystotome in a non-cutting fashion, or the initial capsular incision is torn into a circular shape by grasping the leading edge with fine caliber forceps. This is a very challenging maneuver and even in the most experienced hands, the tearing motion can lead to an undesirable tear of the capsule toward the back of the lens.

Even if a proper tagless edge is produced, the capsular opening's size or position is often not ideal. A small capsular opening can impair the safe removal of the lens nucleus and cortex and prevent proper intraocular lens insertion into the lens capsule. The additional stresses placed on the lens capsule, which results from having to work with a small or eccentric capsular opening, puts the eye at risk for zonular and capsular breakage. Both of these breakages will prolong the operative time and can lead to vitreous loss.

Some of the prior devices used in performing an anterior capsulectomy include manual and mechanical techniques for severing the anterior lens capsule of the eye. For example, U.S. Pat. No. 4,570,632 to Woods describes a cystotome which produces a continuous series of perforations; U.S. Pat. No. 4,706,669 to Schlegel describes a device for perforating the lens capsule by use of a wire which is connected to a drive motor which causes the wire to engage in an auxiliary reciprocating motion; U.S. Pat. No. 4,708,138 to Pazandak describes a manually rotating surgical cutting knife; and U.S. Pat. No. 4,885,004 to Pao describes a rotating cystotome.

In most prior known devices, it is difficult to cleanly cut the capsule without leaving residual "tags" or tears in the capsule. Moreover, these devices either cause sufficient drag on the capsule and rock the nucleus of the lens, or place stress on the zonular structure. More importantly, none of the prior devices allows the surgeon to positively position and control the blade at a desired angular position during the movement of the blade's handle. Rather, the configuration of the lens directs the path and angle of the blade disclosed in the prior devices. In other words, these prior devices are directed passively by frictional contact with the lens substance. In addition, these prior devices require a high level of skill, have a protracted learning time, and a significant amount of experience with these devices is necessary to consistently obtain successful results.

The problem which forms the basis of this invention consists in developing a device that permits the surgeon to make a continuous, smooth, curvilinear cut by manually and positively changing the blade's angle of attack through a controller on the handle. The need to enhance the methods and procedures for performing the anterior capsulectomy during phacoemulsification surgery has become critical to the success of the surgery. As a result of the difficulties and complications discussed above, a definite need exists for a device that allows the surgeon to adjust and control the blade's angle of attack in an efficient, effective and complication-free manner. It is, therefore, a feature of the present invention to provide a capsulectomy apparatus which manually facilitates a continuous, smooth, curvilinear cut.

Another feature of the present invention is to provide a capsulectomy apparatus which does not rock the nucleus of the lens.

An additional feature of the present invention is to provide a capsulectomy apparatus that eliminates residual tags of the anterior capsule.

A further feature of the present invention is to provide a capsulectomy apparatus which easily cuts any desired capsule pattern, at any location, and of any size.

To achieve the above objects, features, advantages, an ophthalmic surgical device is provided which comprises a handle, a blade rotatably mounted to the handle's distal end and a controller on the handle for manually and positively positioning the blade at a desired angular position during movement of the handle. The controller can consist of a variety of different mechanisms such as two opposed jaws that move relative to each other; or a plurality of spools which are connected by a belt; and the rotation of one spool permits the surgeon to control the blade's angle of attack; or an operator and gear train which transmits the operator's motion to the blade. The surgical instrument also includes an orientation mark on the blade which indicates the plane of the cutting blade.

Other objects, advantages, and novel features of the present invention will become apparent from the following detailed description of the invention when considered in conjunction with the accompanying drawings.

BRIEF DESCRIPTION OF THE DRAWINGS

FIG. 1 is a perspective view of a surgical instrument in its disengaged position incorporating the principles of the present invention.

FIG. 2 is a side view of the surgical instrument of FIG. 1 in its engaged position and incorporating the principles of the present invention.

FIG. 3 is a top view of a latching mechanism depicted in FIG. 2.

FIG. 4 is an enlarged view of the handle's distal end holding the blade as depicted in FIG. 2.

DETAILED DESCRIPTION OF THE DRAWINGS

The General Instrument

Figure 5:
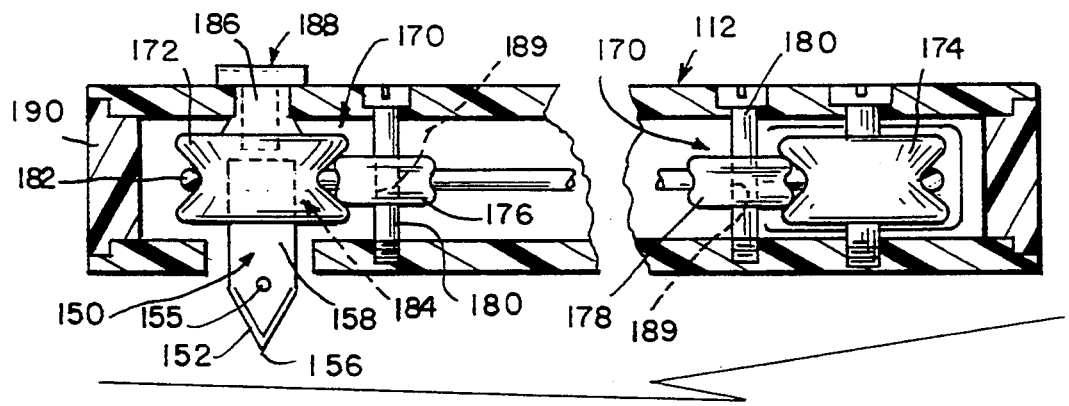
FIG. 5 is a side cut-away view of another embodiment of the surgical instrument containing rotatable spools and belt.

This invention relates to a surgical device which includes a handle 12, 112, 212, blade 50, 150, 250, and controller 70, 170, 270. This invention permits the surgeon through either one hand or two hand manipulation to positively position the blade 50 at a desired angular position during movement of the handle 12. The operation of the instrument 10 is such that the surgeon is able to positively control the blade's angle of attack by moving the handle's jaws relative to each other, or by rotating spools or gears which transmit motion to the blade.

The First Embodiment

Referring to the figures, the surgical instrument is identified generally by the numeral 10. As shown in FIGS. 1 and 2, the first embodiment of the surgical instrument 10 consists of a handle 12, a latching mechanism 30, and a controller 70. FIG. 2 also shows a blade 50. The surgeon controls the blade's angle of attack in this embodiment by manipulating portions of the handle 12 relative to each other. In this embodiment, the handle 12 includes two opposing walls 14 joined at their proximal ends 19 and separated at their distal end to form two blade holding jaws 20. For ease of discussion, the opposing walls 14 will be referred to herein as 14a and 14b. The handle 12 can be manufactured in a variety of shapes and sizes and from a variety of materials such as plastic, steel, aluminum, or any other light weight material. In the preferred embodiment, the handle 12 is shaped from a band of metal into the configuration described herein. For example, the handle 12 could be constructed by taking a 1.0 cm band of thin steel and bending it around so that its distal ends converge towards each other to form jaws 20. In addition, the inner surface of the jaws 20 may be textured. This texturing 23, shown in FIGS. 1 and 4, increases friction between the handle 12 and blade 50. The jaws 20 are parallel to both each other and the direction of the adjusting motion but may not be parallel to the longitudinal axis of the handle 12. It is important to note that while the surgeon moves the instrument 10 in a circular path, he/she also moves the jaws 20 of the opposing walls 14a, 14b relative to each other which causes the blade 50 to rotate either clockwise or counterclockwise. The interaction and relative movement of the opposing walls 14a, 14b characterizes the operation of controller 70.

The handle 12 further includes two platforms 22 for placement of the surgeon's fingers during the surgical procedure. In this embodiment, a platform 22 is placed approximately two-thirds of the distance away from the distal ends on both walls 14a, 14b which enhances the surgeon's ability to move the handle 12 and positively position the blade 50 at a desired angle during movement of the handle 12. The platforms 22 can also be manufactured from a variety of materials such as plastic or metal. The platforms 22 can be attached to the handle 12 in a variety of manners with welding being one of the easier manners.

The jaws 20 of the handle 12 have two positions—a disengaged and engaged position. In the disengaged position, as shown in FIG. 1, the handle's jaws 20 are held together before the handle 12 engages the blade 50 by a cap 61 (shown in FIG. 4) which fits over the distal most tip portions of the jaws 20. FIG. 1 shows a band of metal 24 placed between the jaws 20 in order to prevent the jaws 20 from separating a large amount. The metal band 24 functions to prevent an excessive opening of the jaws 20 in the disengaged position and serves to keep the walls 14a, 14b in the proper orientation as they move past one another during the procedure. The metal band 24 also acts as a spring which encourages the opening of the jaws in the disengaged position. It is the spring of metal band 24 and the handle 12 which is the opposing force to the latching mechanism 30 which provides a secure hold on the cylindrical shaft 58, which in turn secures the blade 50.

Both jaws 20 also contain orientation marks 21 on their surface which helps align the blade 50 with the handle 12. The orientation marks 21 on the top surface of the jaws 20 are placed approximately 1.5 millimeters from the distal ends of the jaws 20 and form a straight line which is perpendicular to the long axis of the instrument when the instrument is in its engaged position. If the instrument is in its disengaged position and not holding the blade 50, the orientation marks 21 form a broken line as viewed from the top of the jaws 20; the instrument can be stored in this configuration. In use, the jaws 20 are placed within the jaw cap 61, as shown in FIG. 4, which allows the jaws to separate the proper amount so that the blade 50 can fit up between their inner surfaces. The jaws 20 are brought down over the blade 50 in such a way that the orientation marks 21 of the jaws 20 form a line with the orientation mark 62 on the top surface of blade 50. The orientation mark 62 of the blade 50 therefore allows for the proper placement of the blade 50 into the jaws 20 and allows the surgeon to keep track of the angle of attack of the cutting surface 52 while in use, since only the top of the blade 50 is seen clearly by the surgeon during capsule cutting. The orientation marks 21 on the jaws 20 are placed at a distance from the distal end of the jaws 20 which ensures the safe rotation of the cylindrical shaft 58 of the blade 50 between the inner surfaces of the jaws 20.

The handle 12 also includes a latching mechanism 30 which functions when the handle 12 is in its engaged position. FIGS. 1 and 2 show the latching mechanism 30 which consists of a slot 32, a receiver 34, and a securing member 36. In this embodiment, the slot 32 is contained on wall 14a. The receiver 34 can be a rolling mechanism which consists of a cylinder 38 and a bracket 40 mounted on wall 14b. The cylinder 38 rolls on a pivot pin 42 wherein the pivot pin 42 is placed through the longitudinal axis of the cylinder 38 and secured to each end of the bracket 40. The cylinder 38 can be manufactured from a variety of materials including plastic or metal. The rolling mechanism serves the purpose of minimizing friction between the latching mechanism 30 and the wall 14a. Hence, the rolling mechanism makes it easier for the surgeon to move walls 14a and 14b relative to each other. The slot 32 is large enough to receive the cylinder 38.

Figure 7:
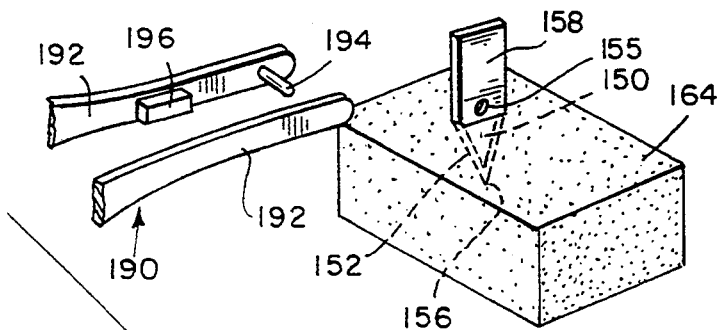
FIG. 7 is a perspective view of a blade contained in its packaging material along with forceps for grasping such blade.

The surgical instrument 10 also includes a blade 50 which is slightly different than the blade 150 illustrated in FIG. 7 and is contained in a styrofoam package 164. The blade 50 can also be manufactured into a variety of shapes and sizes. In this embodiment, the blade 50, as shown in FIG. 4, has a thin and triangular shape with two cutting edges 52 converging to a point at one end 56, a cylindrical shaft 58 at the other end, and a head 60. The shaft 58 can also be textured which will increase the friction between the jaws 20 of handle 12 and the blade 50. The head of the blade 60 also contains the orientation mark 62 on the head's surface. This orientation assists the surgeon in indicating the plane of the cutting edge 52 and facilitates the proper placement of the blade 50 into the jaws 20. The blade 50 can come as a completed structure as described above, or in two pieces which requires surgeon assembly. In the latter embodiment, the blade is separate from cylindrical shaft 58. This embodiment is detailed in the text of the second embodiment. Once assembled, a spool similar to spool 172 with the blade 150 inserted into it can be oriented within the jaws 20 using the orientation mark on the top of the spool 172 and the orientation marks 21 of the jaws 20.

Operation of First Embodiment

In the first embodiment, the blade 50 is removed from a sterile package which differs slightly from the configuration illustrated in FIG. 7. The blade is preferably housed in a block of styrofoam with only the head 60 and a small segment of the shaft 58 exposed above the styrofoam. The handle 12 is then positioned over the head 60. The jaws 20 are held together, preferably by the jaw cap 61. The jaw cap 61 allows the distal end jaws 20 to separate enough distance so that the distal end jaws 20 can be placed over the head 60. The orientation mark on the surface of the head 62—which indicates the plane of the cutting surface below—is positioned at and coaxial to the distal end orientation marks 21.

Once the handle 12 has grasped the blade's shaft 58 below the head 60, the handle 12 is squeezed further until the receiver 34 has protruded through the slot 32 as illustrated in FIGS. 2 and 3. At this point, the securing member 36, which in this embodiment is a sliding metal bar, is pushed forward under the receiver 34 towards the distal end of the slot 32. This part of the operation closes the slot 32 and leaves two longitudinal slats 44 for the bracket 40 to move within.

Once the handle 12 and blade 50 are "locked" (the engaged position), the surgical instrument 10 is used by inserting the blade 50 in a horizontal direction through the scleral or corneal incision into a viscoelastic filled anterior chamber. The surgical instrument 10 is uprighted within the eye and the capsule is punctured at the 6:00 or 12:00 position. The blade 50 is then guided to make a circular or oval capsulotomy which will result in a continuous, smooth, curvilinear, stress-free and tag-free cut. This cut is facilitated by using the orientation mark on the head 62 as a guide to the plane of the cutting edge 52 below.

This invention is unique because it permits the surgeon to manually and positively control and maintain the cutting edge 52 parallel to the cutting surface for the full 360 degrees by positively rotating the blade's cutting plane while forming a circular pattern. The finger platforms 22 facilitate the sliding of the distal end jaws 20. During the surgical procedure, the surgeon will move the surgical instrument 10 in such a way that he/she will be able to make a continuous, smooth, curvilinear cut. The surgeon can positively control the blade's angle of attack by moving walls 14a and 14b relative to each other. For example, FIG. 4 shows that as wall 14a is moved towards the distal end 20, and/or wall 14b moves away from the distal end 20, blade 50 will rotate counterclockwise. Likewise, as wall 14a is moved away from the distal end 20, and/or wall 14b moves toward the distal end 20, the blade 50 will rotate clockwise.

The Second Embodiment

As mentioned previously, the handle can be manufactured in a variety of shapes and sizes in order to solve the problem that forms the basis of this invention—developing a device that permits the surgeon to make a continuous, smooth, curvilinear cut by manually and positively changing the blade's angle of attack through a controller on the handle. FIG. 5 shows another embodiment that permits the surgeon to achieve this objective.

Similar to the first embodiment, FIG. 5 reveals a surgical instrument 10 that consists of a handle 112, a blade 150 and a controller 170 on the handle. In this embodiment, the handle 112 consists of a housing in the shape of a hollow cylinder. The external diameter of the cylinder should be approximately 2-2.5 mm.

FIG. 5 also shows a controller 170 for rotating and maintaining the blade's angle of attack during surgery. The controller 170 consists of a plurality of spools. In this embodiment, the controller 170 consists of four spools, two large spools 172, 174 and two small spools 176, 178. In this embodiment, one large spool is located near both ends of the handle 112. The large spools 172, 174 can be manufactured from a variety of materials including nylon or Teflon. Each spool has a circumferential recess and is configured so as to accommodate a belt 182. The circumferential recess on the large spools 172, 174 is also of sufficient size so that it fits over the small spools 176, 178. The bottom of the large spool 172, which is at the distal end, includes a slot 184 for insertion of the blade 150.

The controller 170 also includes two smaller spools 176, 178 which are located between the two larger spools 172, 174. The smaller spools 176, 178 should have a diameter and length of approximately 2.0 mm and 2.5 mm respectfully. Small spools 176, 178 can also be made from a variety of materials including nylon, Teflon, and metal. The shape of small spools 176, 178 should be such that they fit into the circumferential recess of large spools 172, 174. In this embodiment, small spools 176, 178 have a central axis hole 189 through its length. A separate post 180 is then inserted through the top of the cylinder and the central axis hole 189 where it is eventually secured by a screw thread located at the bottom of the cylinder and at the end of the post 180.

The top of large spool 172 can be threaded to a fastener 186. The surface of fastener 186 contains an orientation mark 188 which is parallel with the slot 184. The fastener 186 helps maintain the large spool's vertical axis of rotation during operation of the surgical instrument 10. The fastener 186 will offer the surgical instrument 10 better support and will also tend to seal off the lumen of the cylinder. If a fastener 186 is not desired, then the top of large spool 172 can simply be marked with a line which is parallel with the slot 184. This can be achieved by leaving an opening in the top of the cylindrical housing over spool 172.

The belt 182 connects large spool 172 to small spool 176 to small spool 178 to large spool 174. The belt 182 should be constructed from a relatively inelastic but flexible material. The belt 182 is positioned around the outer circumferential recess of both large spools 172, 174 and small spools 176, 178. However, the belt 182 only contacts large spools 172, 174. It should be noted that the end closest to the surgeon—containing large spool 174 and small spool 178—is a mirror image of the end farthest from the surgeon with the only differences being that large spool 174 does not contain a slot 184 for a blade 150 and the top of large spool 174 protrudes out of the handle 112 so that the surgeon can rotate the large spool 174 with his fingertips. The interaction between the large spools 172, 174 and the small spools 176, 178 consists of the following. As the surgeon rotates the large spool 174, motion is transmitted to the other spools 178, 176, 172. The surfaces of the pair of large spool 174 and small spool 178 and the pair of large spool 172 and small spool 176 contact each other creating a small amount of friction between these surfaces. While the spools rotate in the same direction, the surfaces of the respective pairs of spools 174, 178 and 172, 176 rotate in opposite directions due to their respective configurations. In other words, the friction between large spool 174 and small spool 178 and large spool 172 and small spool 176 causes small spools 176, 178 to rotate in the opposite direction of large spools 172, 174.

In order to assemble the second embodiment, the handle 112 has the distal cap 190 removed. The belt 182 is inserted into the handle 112. The large spool 174 is inserted into the handle 112 through a cap (not shown) on the proximal end of handle 112. The large spool 174 is placed within the loop of the belt 182 and is affixed to the handle with a separate bolt. The belt is drawn to the distal end of handle 112. Small spools 176, 178 are placed within the loop of belt 182 and secured to the handle 112 with post 180. The large spool 172 is placed within the loop of belt 182 and is drawn against small spool 176, which is drawn to the middle of the handle 112 by riding in the circumferential recess of large spool 172. The large spool 172 is further secured by the screwing of fastener 186 into the top of large spool 172. The terminal caps are returned to the distal and proximal ends, respectively, of handle 112. The large spool 172 is now ready for blade 150 insertion and instrument use.

FIG. 7 shows a blade 150. In this embodiment, the blade 150 consists of a flat band of steel which is sharpened on both sides to create two cutting edges 152. The cutting edges 152 converge to form a point 156. Each cutting edge 152 should be sharpened for a length of approximately 1.5 mm. The cutting edges 152 also extend to the blade's top portion or shaft 158 which takes on a rectangular shape. A hole 155 is placed near the junction of the cutting edges 152 and the blade's shaft 158. The hole 155 will assist in the insertion of the blade 150 from the styrofoam package 164 to the large spool 172 and will be discussed herein. It should be noted that the blade 50 in FIG. 2 can be replaced by a spool similar to the spool 172 and rectangular blade 150 combination of FIG. 5. This will allow the use of standard blades having rectangular shafts instead of special blades having cylindrical shafts.

In an alternative embodiment, only three spools are required to be linked by the belt 182. Distally, two spools are required, a large spool 172 and a smaller spool 176. The smaller spool 176 helps to keep the rotational movement of large spool 172 smooth and prevents its translocation proximally from forces generated by the belt 182. On the proximal end, the large spool 174 can be affixed to the handle 112 with a separate bolt directed through a central axis hole. In this configuration, the belt 182 unites the spools frictionally, and the two distal spools 172 and 176 are likewise frictionally united. Rotation of large spool 174 thus positively controls the attack angle of the blade 150 which is inserted into spool 172.

Operation Of Second Embodiment

The handle 112 includes at least two spools, a large spool 172 and small spool 176.

The blade 150 is initially packaged in styrofoam housing 164 with the top rectangular portion 158 and hole 155 exposed from the styrofoam 164. The surgeon takes a forceps 190 which superficially resembles a Kellman-McPherson forceps distally and has approximately the same proportions. There are two modifications on the inside of one arm 192. One modification is the placement of a post 194 which will fit through the hole 155 on the top rectangular portion of the blade 158. The other modification is the placement of a small block 196 which has a flat face and is positioned a proper distance from the post 194 such that it will be flush with the blade's short lateral rectangular portion 158 when the forceps 190 are closed. The forceps 190 can be made to lock in the standard fashion of a locking needle holder. Once the blade 150 is secured by the forceps 190, the surgeon will lift the blade 150 from the styrofoam for insertion into a slot 184 of large spool 172. The opening of the slot 184 is slightly smaller than the width of the blade's top rectangular portion 158 such that when the blade 150 is inserted into the slot 184, the blade 150 is held securely by friction or a press fit.

Once the blade 150 is positioned over a portion of the anterior capsule which is parallel to the plane of the blade, the surgeon exerts a small amount of force such that the blade 150 punctures the anterior capsule at this point. The surgeon then traces the desired shape of the capsular opening while rotating the large spool 174 at the proximal end. Because the spools are coupled by belt 182, the large spool 174 will control large spool 172 and the blade's 150 angle of attack. For example, by rotating the large spool 174 counterclockwise, the other spools, 178, 176, 172 and blade 150, rotate in the same direction. This allows the surgeon to make a continuous, smooth, curvilinear, stress-free, tag-free cut. The blade 150 fits tightly into the slot 184 so that when the large spool 172 is positively rotated about its vertical axis, the plane of the blade follows it without slipping within the axis of the spool. As spool 172 is rotating, the plane of the blade below can be tracked by watching the orientation mark on the top of the spool 172 through the opening in the housing. As an alternative to manipulating spool 174 from the top by a different hand than the hand that guides the instrument 10, large spool 174 may extend laterally beyond the housing allowing manipulation by the thumb of the guiding hand.

The Third Embodiment

Figure 6:
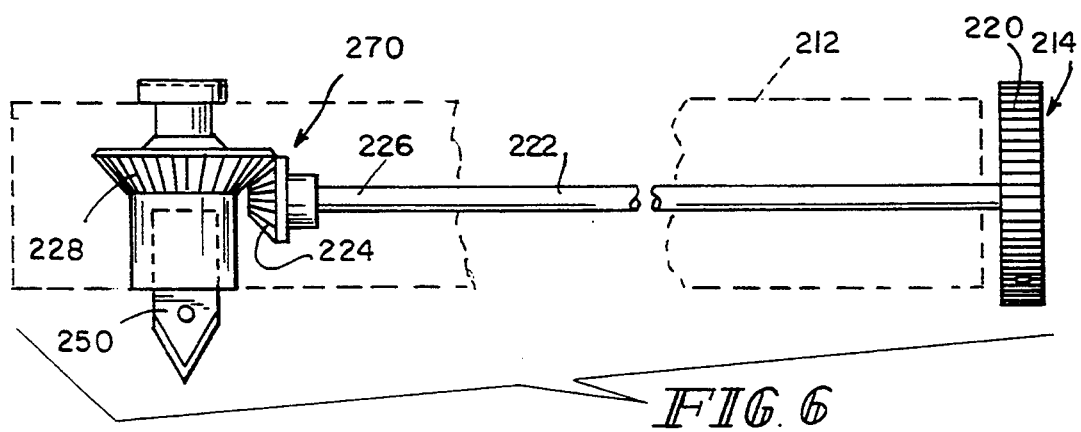
FIG. 6 is a side view of another embodiment of the surgical instrument containing rotatable gears.

FIG. 6 shows an alternative embodiment for the controller. Instead of a belt 182 and pulley transmission, a gear transmission is utilized. In this embodiment, the handle 212 can be shaped like a cylinder which is shown in dashed lines. The controller 270 includes an operator 214 and a gear train connecting the operator 214 to the blade 250 to transmit motion of the operator 214 to rotation of the blade. The manner in which the operator 214 transmits such motion can take on a variety of forms. FIG. 6 discloses a controller 270 which includes a knob 220, a shaft 222, a first gear 224 attached to the distal end 226 of the shaft, and a second gear 228 engaging the first gear 224. Gears 224, 228 should be made of a lightweight material such as plastic. As shown in FIG. 6, first gear 224 is perpendicular to second gear 228. Such gears are referred to as miter or crown gears. In order to obtain more efficient meshing, bevel gears may be provided with spiral teeth instead of straight teeth. A blade 250 is attached to second gear 228 such that rotation of second gear 228 causes the blade 250 to rotate to the desired angular position. Gear 228 may have a slot for insertion of the blade 250. This type of connection is similar to the arrangement shown in FIG. 5 where a receiving spool is housed within second gear 228 which has a slot within it to receive the insertion of rectangular blade 150 by forceps 190. Alternatively, a blade within a spool similar to blade 50 could be inserted into a lumen within the second gear 228 from below with forceps 190.

Operation of the Third Embodiment

The controller 270 of this embodiment operates in the following manner. First, a blade 250 is inserted into second gear 228. Once the surgical instrument 10 is uprighted within the eye and the capsule is punctured at the 6:00 or 12:00 position, the surgeon will begin to rotate the knob 220. The rotation of the knob 220 causes gear 224 to rotate gear 228 and blade 250 in the same direction as knob 220. This controller 270 permits the surgeon to manually and positively position the blade's cutting angle at a desired angular position.

This invention is unique and novel in that it permits the surgeon to manually and positively position the blade at a desired angular position during movement of the instrument's handle. The inventive controller can take on a variety of shapes and configurations. The first embodiment discloses a controller 70 wherein the surgeon is able to move the jaws 14a, 14b relative to each other. The second embodiment discloses a controller 170 which includes a plurality of spools wherein the rotation of one spool 174 transmits motion to the other spools 178, 176, 172 and the blade 150. The third embodiment discloses a controller 270 which includes a gear transmission which transmits motion to the blade 250. The controller in each embodiment allows the surgeon to make a continuous, smooth, curvilinear, stress-free, tag-free cut of the anterior capsule.

While there are shown and described present preferred embodiments of the invention, it is to be distinctly understood that the invention is not limited thereto, but may be otherwise variously embodied and practiced within the scope of the following claims.

What is claimed:

1. A hand-held surgical instrument for use in performing a continuous, smooth, curvilinear, stress-free, tag-free cut comprising:
   a handle consisting of two opposed jaws at a distal end of said handle;
   a blade rotatably mounted to the handle's distal end; and
   a controlling means on the handle for manually and positively positioning the blade's cutting angle at a desired angular position during movement of the handle by moving the jaws relative to each other along an axis parallel to the jaws to positively position the blade's cutting angle.

2. The surgical instrument of claim 1, including a visible orientation mark associated with the cutting blade and which indicates the plane of the cutting blade.

3. The surgical instrument of claim 1, wherein the handle includes an orientation mark for initial alignment of the angle of the blade.

4. The surgical instrument of claim 1, wherein the handle includes a pair of finger platforms which helps the surgeon move the instrument.

5. The surgical instrument of claim 1, wherein the blade has a round shaft and said blade is secured between the jaws.

6. The surgical instrument of claim 1, wherein the blade is a rectangular shaft and said blade is inserted into a spool and rotatably mounted between the jaws.

7. The surgical instrument of claim 1 further comprising a latching mechanism for locking the jaws distal ends in a closed position.

8. The surgical instrument of claim 7, wherein the latching mechanism includes:
   a receiver on a first jaw for placement through a slot;
   a slot on a second jaw for accepting the receiver; and a securing member for locking the receiver in said slot.

9. The surgical instrument of claim 8, wherein the securing member is a sliding bar.

10. The surgical instrument of claim 8, wherein the receiver includes:
a bracket in said first jaw; and
a cylinder and a pivot pin mounting said cylinder to said bracket.

* * * * *

UNITED STATES PATENT AND TRADEMARK OFFICE
CERTIFICATE OF CORRECTION

PATENT NO. : 5,423,841
DATED : June 13, 1995
INVENTOR(S) : Michael S. Korenfeld

It is certified that error appears in the above-indentified patent and that said Letters Patent is hereby corrected as shown below:

On the title page, item [75]:

Please change the inventor's name and address from:

Michael S. Kornefeld
10332 Sannios, Apt. 5
St. Louis, Mo. 63146 to

Michael S. Korenfeld
10332 Sannois, Apt. 5
St. Louis, MO. 63146

Signed and Sealed this

Fifth Day of September, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,423,841
DATED : June 13, 1995
INVENTOR(S) : Michael S. Korenfeld

It is certified that error appears in the above-indentified patent and that said Letters Patent is hereby corrected as shown below:

On the Title page, item [76]:
Please change the inventor's name from:

"Michael S. Kornefeld"

to

--Michael S. Korenfeld--.

Signed and Sealed this

Second Day of April, 1996

BRUCE LEHMAN

*Attest:*

*Attesting Officer*     *Commissioner of Patents and Trademarks*

UNITED STATES PATENT AND TRADEMARK OFFICE
CERTIFICATE OF CORRECTION

| | |
|---|---|
| PATENT NO. | : 5,423,841 |
| APPLICATION NO. | : 08/212932 |
| DATED | : June 13, 1995 |
| INVENTOR(S) | : Michael S. Korenfeld |

It is certified that error appears in the above-identified patent and that said Letters Patent is hereby corrected as shown below:

The name of the inventor is spelled incorrectly on the published patent. On the Title Page, Item (76) please change the inventor name from Kornefeld to Korenfeld. Please make this change for this patent anywhere this name appears.

Signed and Sealed this

Sixth Day of July, 2010

David J. Kappos
*Director of the United States Patent and Trademark Office*